(12) United States Patent
Coronel et al.

(10) Patent No.: US 10,456,439 B2
(45) Date of Patent: Oct. 29, 2019

(54) NK3 AGONIST FOR USE IN THE TREATMENT OF A PATIENT SUFFERING FROM ATRIAL ARRHYTHMIA OR FIBRILLATION

(71) Applicant: ACADEMISCH MEDISCH CENTRUM, Amsterdam (NL)

(72) Inventors: Ruben Coronel, Abcoude (NL); Marieke Veldkamp, Leiden (NL)

(73) Assignee: Academisch Medisch Centrum, Amsterdam (NL)

( * ) Notice: Subject to any disclaimer, the term of this patent is extended or adjusted under 35 U.S.C. 154(b) by 144 days.

(21) Appl. No.: 15/518,553

(22) PCT Filed: Oct. 16, 2015

(86) PCT No.: PCT/EP2015/073956
§ 371 (c)(1),
(2) Date: Apr. 12, 2017

(87) PCT Pub. No.: WO2016/059191
PCT Pub. Date: Apr. 21, 2016

(65) Prior Publication Data
US 2019/0015471 A1    Jan. 17, 2019

(30) Foreign Application Priority Data

Oct. 16, 2014    (EP) .................... 14189212

(51) Int. Cl.
*A61K 38/22* (2006.01)
*A61K 38/04* (2006.01)
*A61K 9/00* (2006.01)

(52) U.S. Cl.
CPC .......... *A61K 38/046* (2013.01); *A61K 9/0019* (2013.01); *A61K 9/0053* (2013.01)

(58) Field of Classification Search
CPC ....................................................... C07K 7/22
See application file for complete search history.

(56) References Cited

U.S. PATENT DOCUMENTS

| | | | | |
|---|---|---|---|---|
| 6,214,810 B1 * | 4/2001 | Fermini | ................. | A61K 31/00 514/137 |
| 2004/0023960 A1 * | 2/2004 | Huskey | ................. | A61K 31/09 514/236.2 |

FOREIGN PATENT DOCUMENTS

| | | |
|---|---|---|
| WO | 02/19966 A2 | 3/2002 |
| WO | 2009/046872 A2 | 4/2009 |

OTHER PUBLICATIONS

Rupniak et al., Neuropsychopharmacology: the fifth Generation of progress, Edited by K.L. Davis et al., 2002, p. 169-177.*
Roccon, Alain et al., "Study of SR 142801, a new potent non-peptide NK3 receptro antagonist on cardiovascular responses in conscious guinea-pig", British Journal of Pharmacology, Jul. 1, 1996, pp. 1095-1102, vol. 118, No. 5.
Wang, Li-Li et al., "Esmolol activates endogenous neurokinin activity inhibiting infarction-induced arrhythmias in rats: Novel mechanisms of anti-arrhythmia", Regulartory Peptides, Sep. 1, 2013, pp, 116-122, vol. 186.
Guler, Niyazi et al., "Do Cardiac Neuropeptides Play a Role in the Occurrence of Atrial Fibrillation After Coronary Bypass Surgery?", The Annals of Thoracic Surgery, Jan. 24, 2007, pp. 532-537, vol. 83, No. 2, Elsevier, United States.
Yu, Yang et al., "Parasympathetic and substance P-immunoreactive nerve denervation in atrial fibrillation models", Cardiovascular Pathology, Jan. 11, 2011, pp. 39-45, vol. 21, No. 1, Elsevier Science, New York, NY, US.
Flynn, Francis W., "Intraventricular injections of tachykinin NK3 receptor agonist reduce the gain of the baroreflex in unrestrained rats", Experimental Neurology, May 1, 2005, pp. 118-124, vol. 193, No. 1, Academic Press, New York, NY, US.
Geuzebroek, S.C. Geuzebroek et al., "Neuropeptide Substance-P Modulates Electrical Characteristics of RabbitAtrial Myocytes", 1448-POS, Feb. 4, 2013, XP026964845.
International Search Report and Written Opinion of International Patent Application No. PCT/EP2015/073956 dated Jan. 14, 2016.

* cited by examiner

*Primary Examiner* — Gyan Chandra
(74) *Attorney, Agent, or Firm* — McBee Moore Woodward & Vanik IP, LLC

(57) ABSTRACT

The invention relates to an NK3 agonist or a pharmaceutically acceptable salt or solvate thereof, for use in the treatment of a atrial arrhythmia. The invention further relates to a composition comprising an NK3 agonist for use in the treatment of a patient suffering from a disease wherein the electrical activity of an atrial heart cell is affected.

20 Claims, 12 Drawing Sheets
Specification includes a Sequence Listing.

Fig. 1 A-F
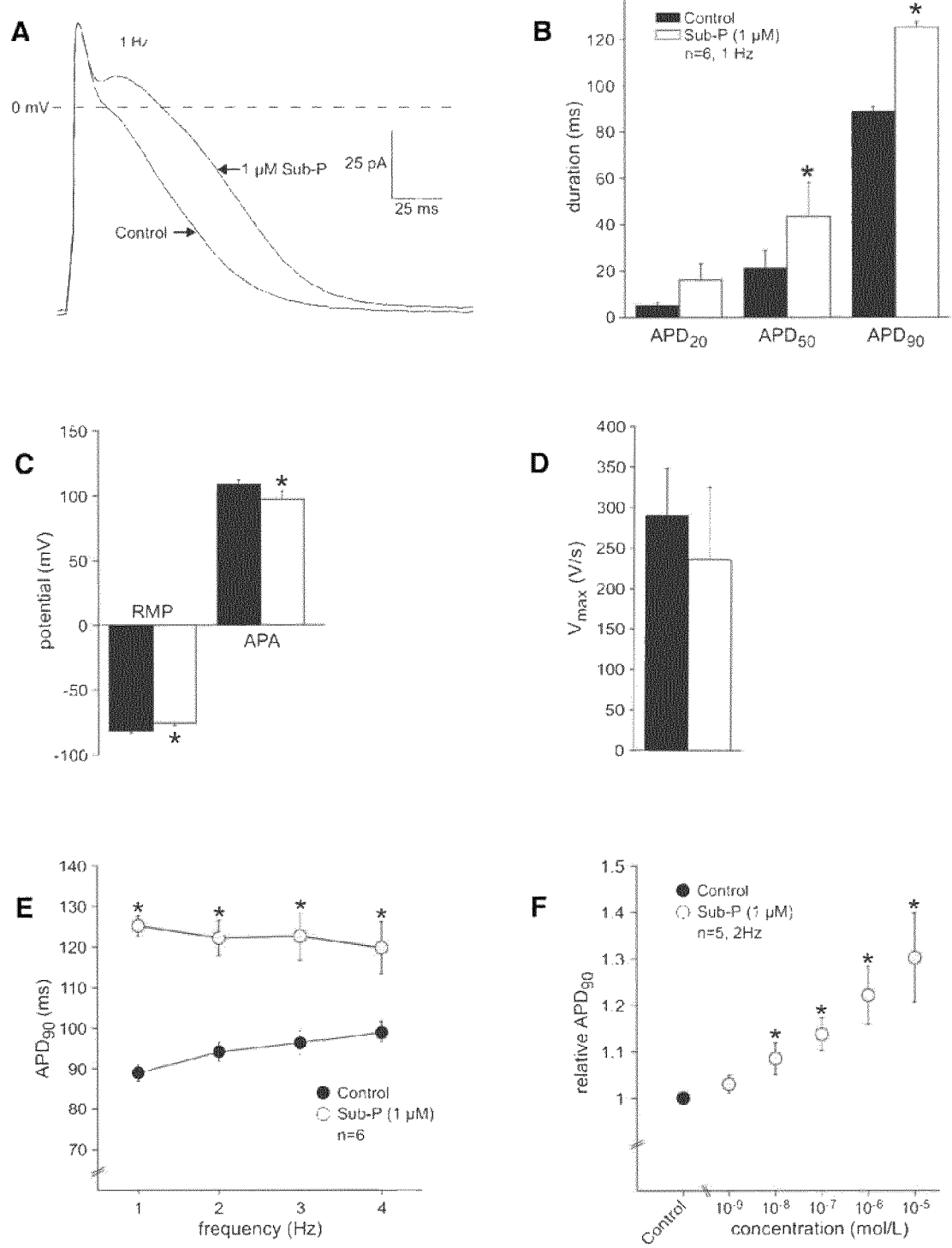

Fig. 2 A-D
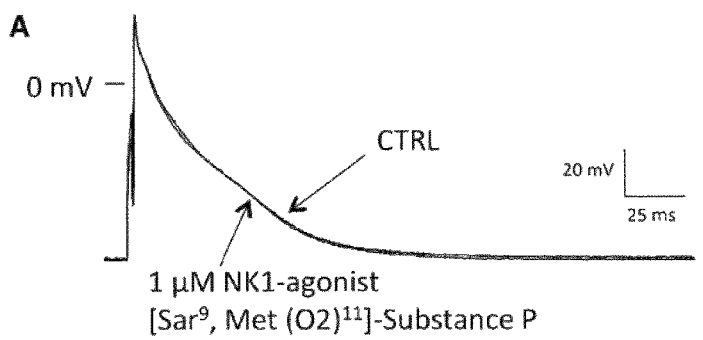
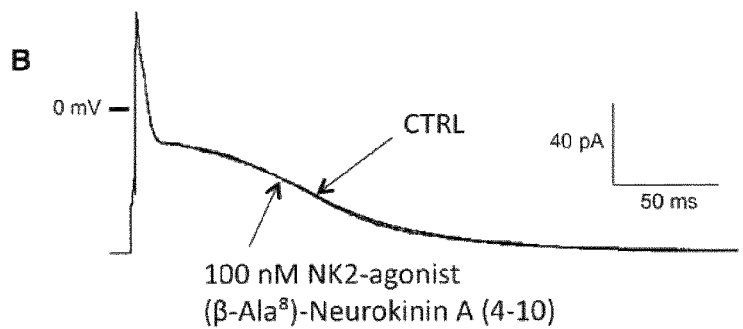
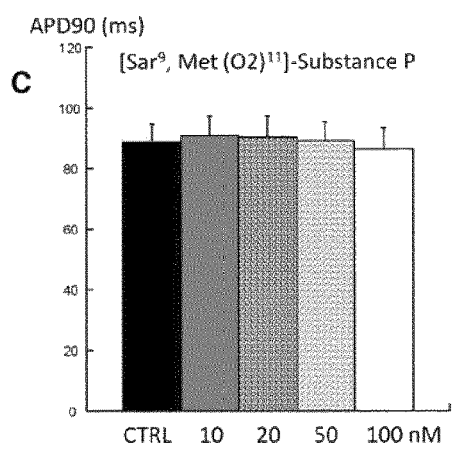
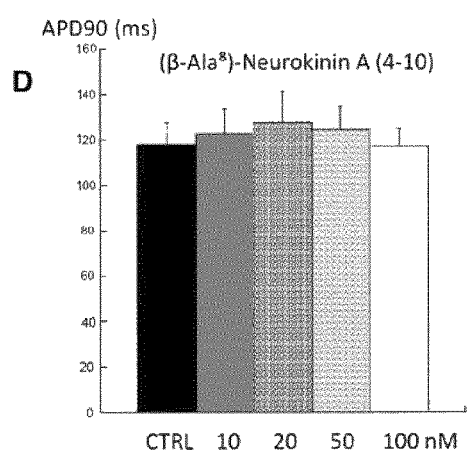

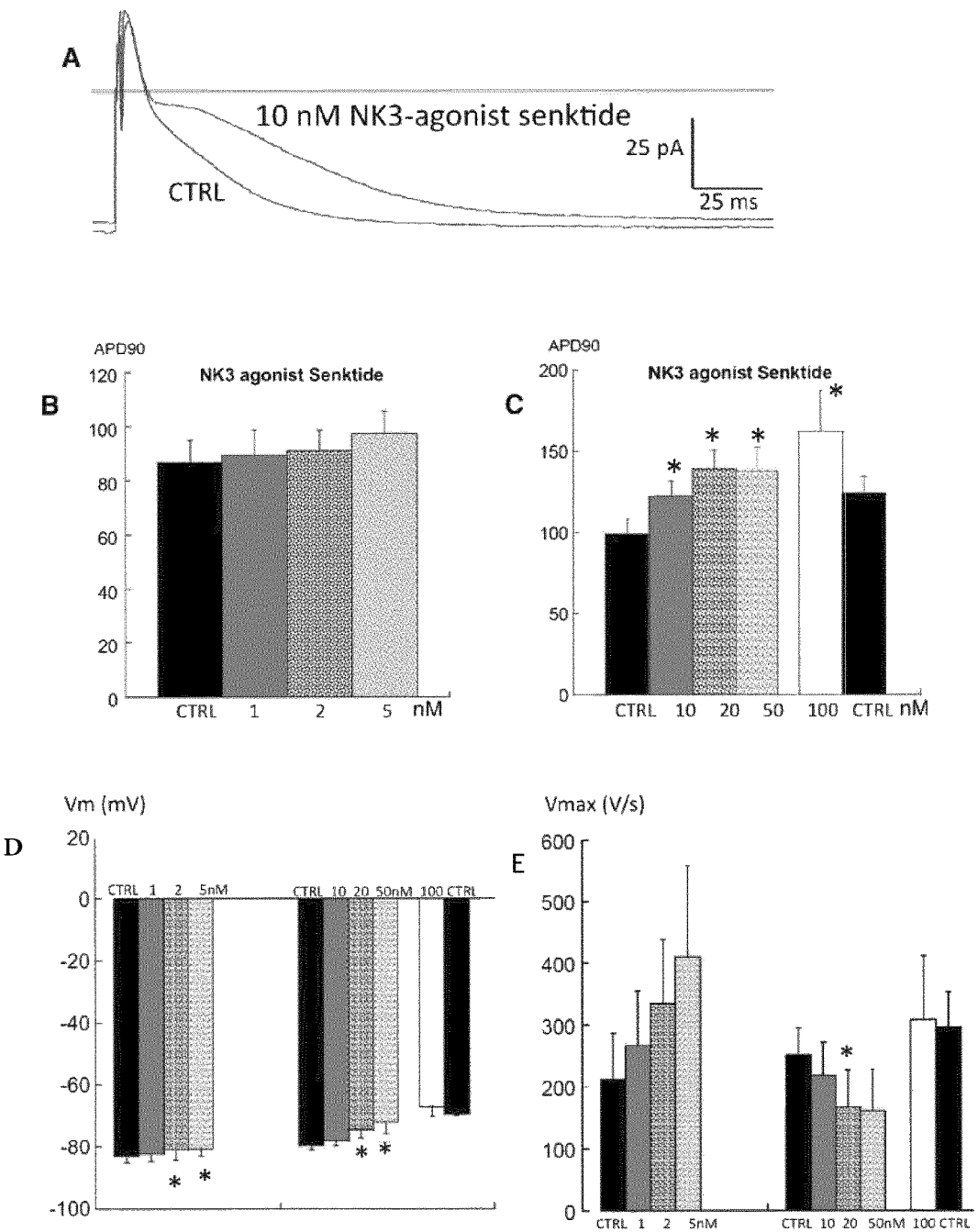
Fig. 3 A-E

Fig. 5 A-D
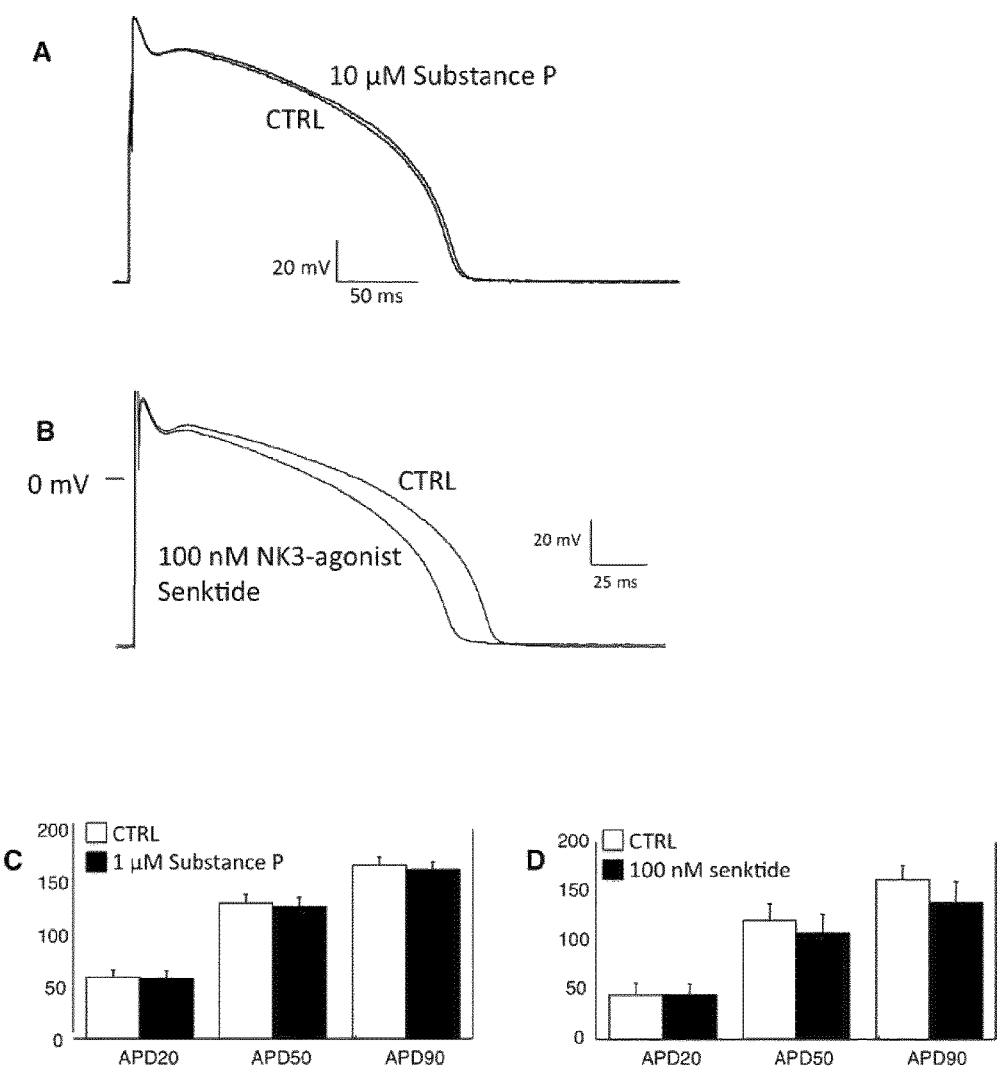

Fig. 6 a-d
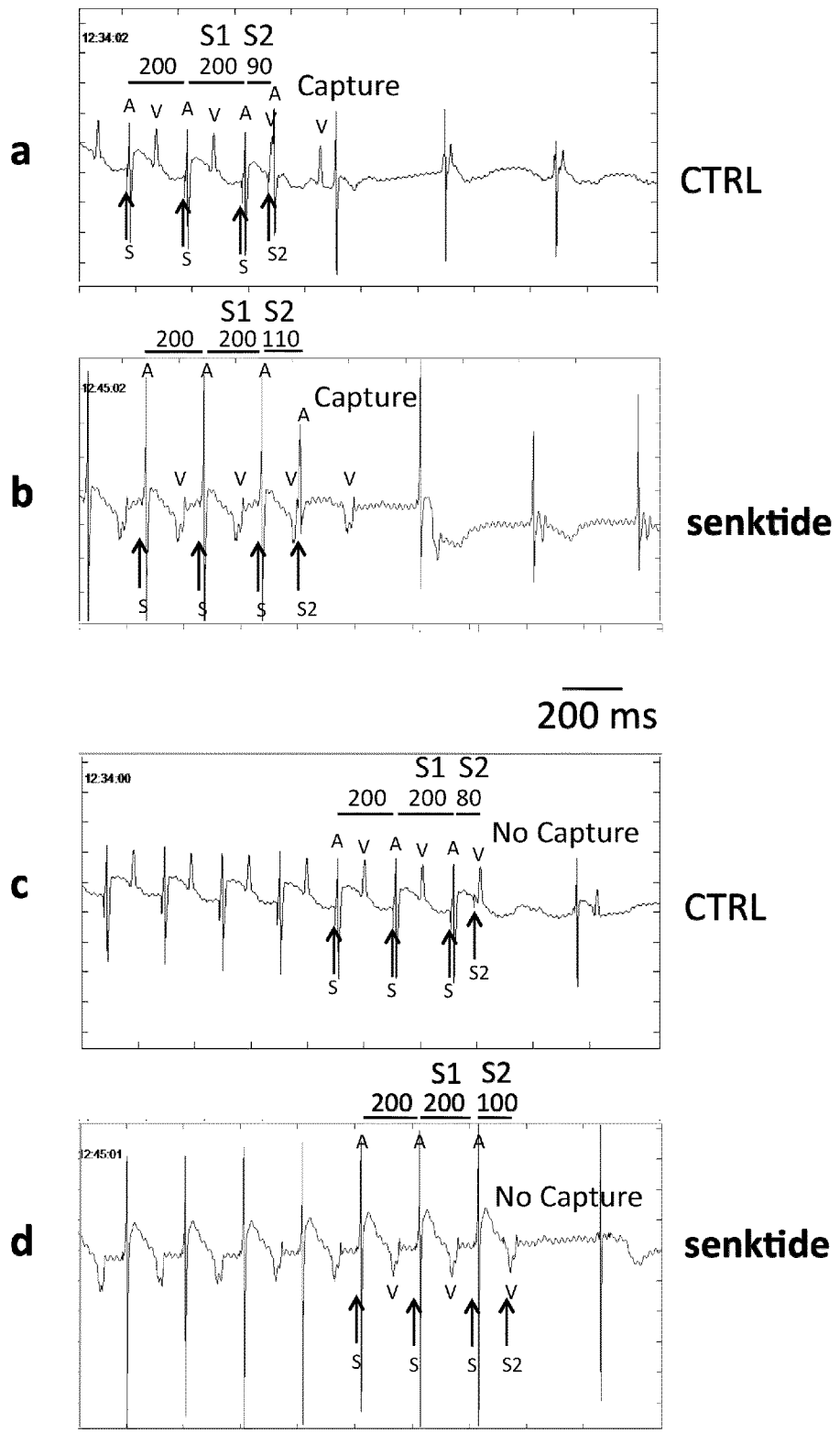

Fig. 7A-D
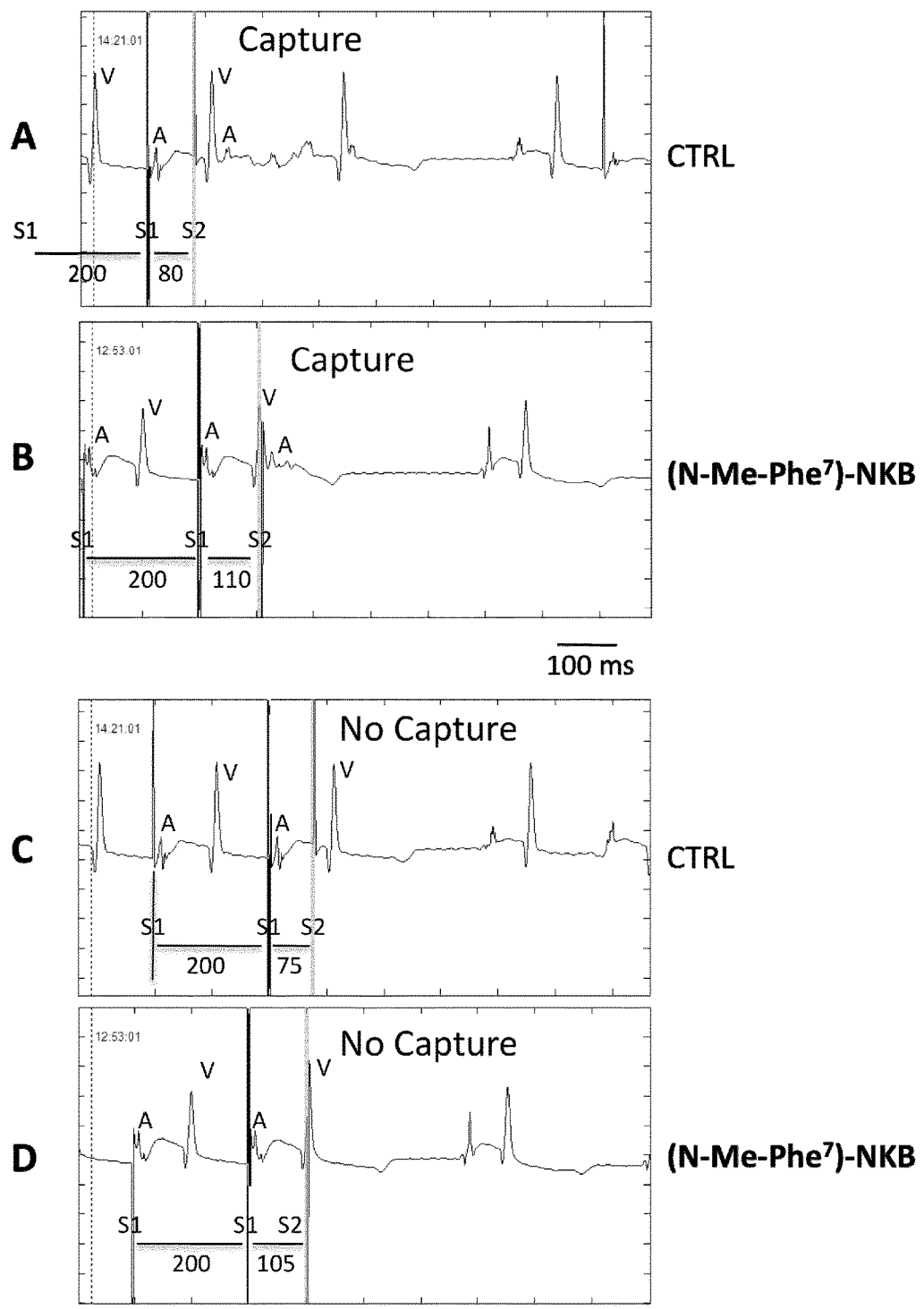

Fig. 8 A-D
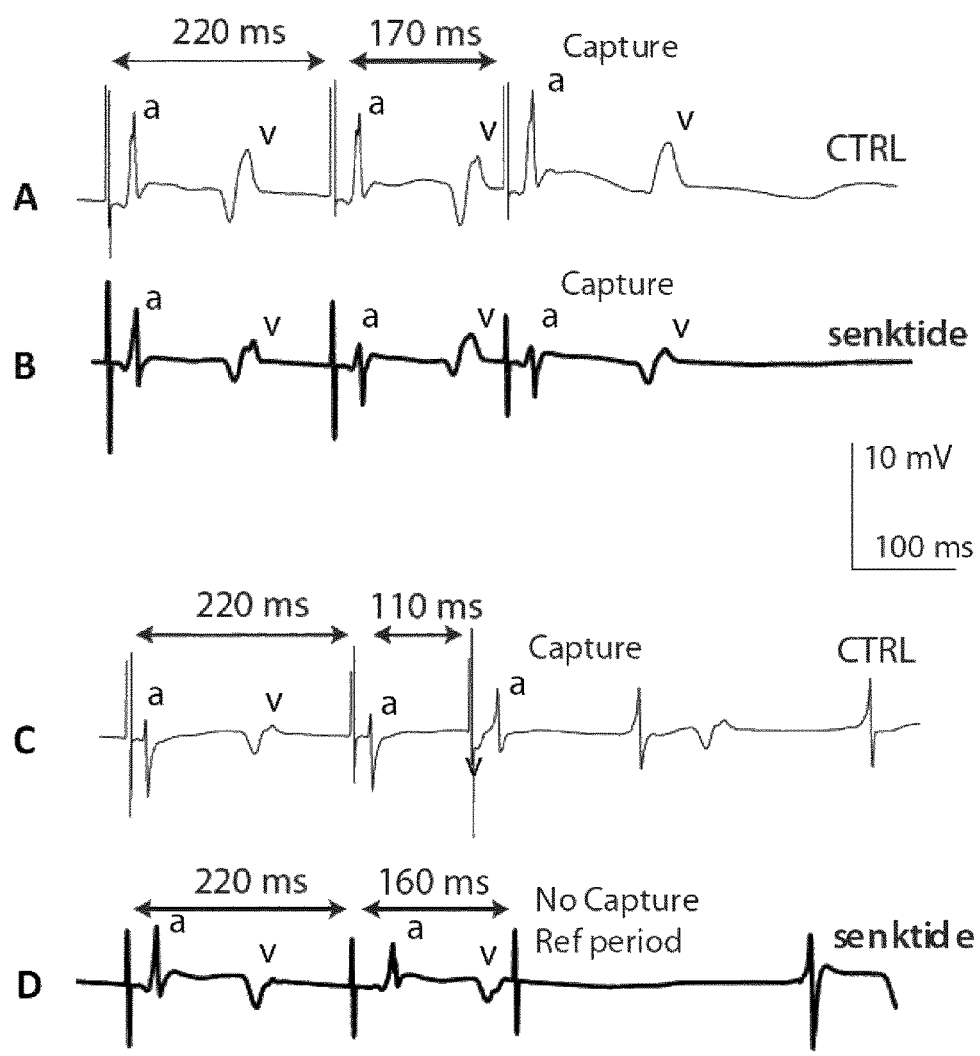

Fig. 9 A, B
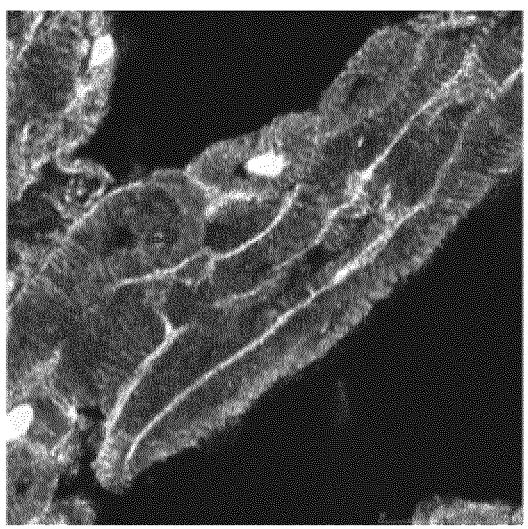
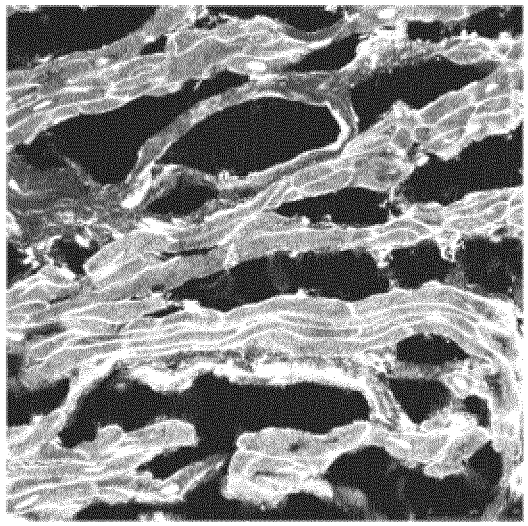

Fig. 10 A, B
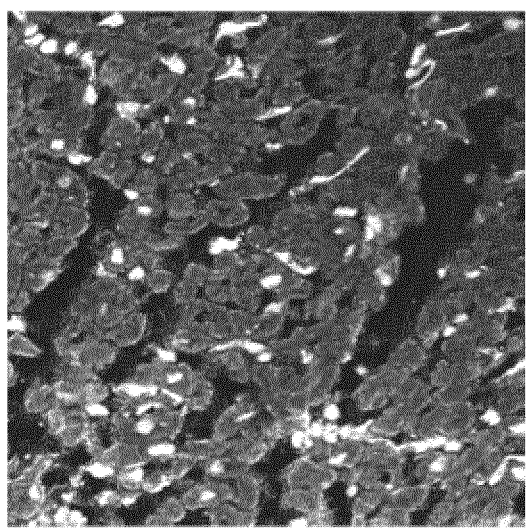
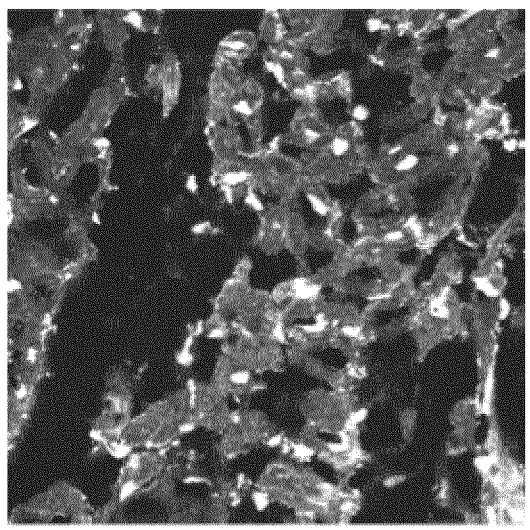

SEQUENCE LISTING

```
<160> NUMBER OF SEQ ID NOS: 3

<210> SEQ ID NO 1
<211> LENGTH: 10
<212> TYPE: PRT
<213> ORGANISM: Homo sapiens

<400> SEQUENCE: 1

Asp Met His Asp Phe Phe Phe Gly Leu Met
1               5                   10

<210> SEQ ID NO 2
<211> LENGTH: 11
<212> TYPE: PRT
<213> ORGANISM: Homo sapiens
```

```
-continued

<400> SEQUENCE: 2

Arg Ser Arg Thr Arg Gln Phe Tyr Gly Leu Met
1               5                   10

<210> SEQ ID NO 3
<211> LENGTH: 10
<212> TYPE: PRT
<213> ORGANISM: Homo sapiens

<400> SEQUENCE: 3

Asp Met His Asp Phe Phe Val Gly Leu Met
1               5                   10
```

NK3 AGONIST FOR USE IN THE TREATMENT OF A PATIENT SUFFERING FROM ATRIAL ARRHYTHMIA OR FIBRILLATION

CROSS REFERENCE TO RELATED APPLICATIONS

This application is a US National Stage Application of PCT Application No. PCT/EP2015/073956, filed 16 Oct. 2015, which claims the benefit of European Application No. EP14189212.5, filed 16 Oct. 2014.

BACKGROUND

Technical Field of the Invention

This invention relates generally to compounds, compositions and methods useful in treating or preventing atrial fibrillation. In particular, the invention relates to NK3 agonists or pharmaceutically acceptable salts or solvates thereof.

Description of Related Art

Atrial fibrillation (AF) is the most common cardiac arrhythmia in the elderly population. In normal sinus rhythm, the atria (the upper chambers of the heart) contract, the valves open, and blood fills the ventricles (the lower chambers). The ventricles then contract to complete the organized cycle of each heart beat and effectuate an efficient ejection of blood into the aorta. AF involves an abnormality of electrical impulse formation and conduction that originates in the atria causing the atria to quiver or fibrillate instead of beat effectively. The heart normally contracts (beats) 60 to 80 times per minute at rest. In AF, the atria fibrillate as many as 300-600 times/minute. During AF, the blood is not able to empty efficiently from the atria into the ventricles with each heart beat. As a consequence, the function of the heart as a pump is reduced and the adaptation of heart rate to exercise is absent. Complications of AF include congestive heart failure and cardiomyopathy. Also, blood may become stagnant in the atria, creating a site for blood clot formation. Such clot formation may become a primary source of stroke in patients with AF. Thus AF, increases the risk of heart failure and stroke and is associated with a poorer performance of the heart as a pump.

Atrial fibrillation is a complex arrhythmia that is associated with structural and functional changes in the atrial tissue and is heavily modulated by the autonomic nervous system. There are two mechanisms of atrial fibrillation that may be operative at the same time: re-entry in the atrial myocardium and spontaneous firing from the pulmonary veins.

AF may be chronic or paroxysmal. In chronic or persistent AF, the atria fibrillate all of the time. In paroxysmal AF, the patient experiences intermittent episodes of AF that occur with varying frequency and last for a variable period of time before spontaneously reverting to normal between episodes.

AF may occur in patients with any type of underlying structural heart abnormality, such as coronary artery disease, valvular heart disease, congenital heart disease, and cardiomyopathies of various kinds, thereby complicating patient management and therapy. In addition, AF occurs in as many as 50% of patients undergoing cardiac operations. Further, AF may sometimes occur in patients with no known underlying structural abnormalities (lone AF) or in patients with lung disease or hormonal or metabolic disorders. AF may occur at any age, but its prevalence tends to increase with age and affects men slightly more often than women. The occurrence of AF may exacerbate other disorders, for example, myocardial ischemia or congestive heart failure.

Many conditions have been associated with AF, including thyroid disorders, valve disease, hypertension, diabetes, sick sinus syndrome, pericarditis, lung disease, and congenital heart defects.

Patients with chronic AF may suffer from symptomatic tachycardia or low cardiac output, have a risk of thromboembolic complications, and are at risk for death.

Several approaches are used to treat and prevent atrial fibrillation. A number of invasive surgical procedures are used for treatment of AF. Invasive procedures involving direct visualization of the tissues include the Maze procedure, in which the atria are surgically dissected and then repaired. In the Maze procedure, for example, ectopic re-entry pathways of the atria are interrupted by the scar tissue formed. The pattern of scar tissue then prevents the recirculating electrical signals that result in AF (reentry) on one hand, and isolates the tissue from which the triggers emanate (the pulmonary veins) on the other.

Radiofrequency energy has been used to terminate atrial arrhythmia or AF by introducing a catheter into the heart and directing a burst of radiofrequency energy to specific areas of the heart to destroy tissue that triggers abnormal electrical signals or to block abnormal electrical pathways (ablation therapy). In addition, surgery may be used to disrupt electrical pathways that generate atrial arrhythmia or AF.

Invasive therapies for atrial arrhythmia or AF have a limited efficacy and often require repetition. Non-invasive, pharmacological treatment of atrial arrhythmia or AF that have long-term efficacy clearly are the preferred method but up to now are associated with severe side-effects. Many anti-arrhythmic drugs have common side effects that involve life-threatening arrhythmias that originate from the cardiac ventricular myocardium. These drugs have in common that they cause a prolongation of the atrial action potential. Prolongation of the atrial action potential with concomitant increase in the effective refractory period is considered anti-arrhythmic in re-entrant arrhythmias. Prerequisite for an effective anti-arrhythmic action of action potential-prolonging drugs is that they are atrial-specific and principally active at high heart rates. However, most of the available anti-arrhythmic drugs for the treatment of atrial arrhythmia also prolong ventricular repolarisation, with consequent life-threatening ventricular arrhythmias. Besides, they may display reverse rate-dependence, being mainly efficacious at lower heart rates, whereas their activity is specifically required at high heart rates. There is, therefore, a need for drugs which do not have one or more of these disadvantages.

SUMMARY OF THE INVENTION

The present invention is based on the surprising finding that NK3 agonists have a direct and specific prolonging effect on the atrial action potential, and do not affect the action potential from ventricular myocardium. In addition, the action potential prolonging effect is also present at high heart rates.

The inventors have shown an increase in atrial effective refractory period in-vivo in an anesthetized rabbit after infusion of the NK3-agonist Senktide (see FIG. 8A-D). In addition, they have shown an increase in the atrial effective refractory period in a rabbit Langendorff-perfused intact heart after application of the NK3-agonist Senktide (FIGS.

6A-E) and (N-Me-Phe[7])-NKB (FIG. 7A-D). Application of Senktide prolongs the S1-S2 interval measured in the left atrium by 20 ms (FIG. 6A-D). Application of NK3 agonist (N-Me-Phe[7])-NKB also prolongs the S1-S2 interval by 30 ms (FIG. 7A-D). The isolated perfused heart according to Langendorff has served as a robust model for many fundamental discoveries in cardiac physiology, pathology and pharmacology for more than 100 years. It is still one of the most widely used experimental designs in cardiovascular research and cardiovascular pharmacology. The model has clear and accepted clinical relevance (see M. Skrzypiec-Spring et al./J. of Pharmacological and Toxicological Methods 55 (2007) 113-126).

Without wishing to be bound by theory, the inventors believe that the prolonging effect on the atrial action potential is due to the inhibition of a background potassium current, which is mediated via compounds which have an agonistic effect on the NK3 receptor. The inventors have shown the expression and localization of the neurokinin-3 receptor (NK3R) in left human atrial appendage (FIG. 9). Based on in vitro experiments using rabbit atrial myocytes, it was hypothesized that Substance P may be beneficial to the prevention and termination of atrial fibrillation (Guillaume S. C et al., internet publication "Neuropeptide Substance-P Modulates Electrical Characteristics of Rabbit Atrial Myocytes", 1448-POS, 4 Feb. 2013 (2013-02-04)). Substance P is an agonist of multiple neurokinin receptors, including NK1R, NK2R and NK3R. This document fails to disclose a treatment using Substance P. Therefore, it was unknown which neurokinin receptor was involved the modulation of the electrical characteristics of the rabbit atrial myocytes. Therefore, this document does not suggest the use of any NK3 agonist for the use in the prevention and termination of atrial fibrillation.

Disclosed herein are compounds, compositions and methods for the treatment or prevention of atrial fibrillation (AF).

The invention provides an NK3 agonist or a pharmaceutically acceptable salt thereof, for use in the treatment of an atrial arrhythmia. The observed prolongation of the atrial action potential is antiarrhythmic against reentrant arrhythmias. In a preferred embodiment, said atrial arrhythmia is a re-entry based atrial arrhythmia, preferably selected from the group consisting of atrial fibrillation, atrial flutter, and atrial tachyarrhythmia.

In a preferred embodiment, the NK3 agonist for use according to the invention has an affinity (pKi) for the NK3 receptor (NK3R) which is higher than 5.0, 5.1, 5.2, 5.3, 5.4, 5.5, 5.6, 5.7, 5.8, 5.9, 6.0, 6.1, 6.2, 6.3, 6.4 or 6.5. Preferably, said NK3 agonist has a pKi for NK1R lower than 11.7, more preferably lower than 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5. In an other preferred embodiment, the NK3 agonist of the invention has a pKi for NK2R lower than 9.1, more preferably lower than 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0. In a highly preferred embodiment, the NK3 agonist is selected from the group consisting of Neurokinin B (NKB), Neurokinin A (NKA), Substance P (SP), Hemokinin 1 (HEK1), Eleodoisin, Kassinin, Senktide [succinyl-(Asp6, MePhe8)-SP(6-11)], [Phe(Me)[7]]-NKB (1a) and [Pro][7]-NKB. Preferably, said NK3 agonist is selected from the group consisting of Neurokinin B (NKB), [Pro][7]-NKB, Neurokinin A (NKA) and Senktide.

The invention further provides a composition comprising an NK3 agonist as defined above and a pharmaceutically acceptable carrier for use in the treatment of an atrial arrhythmia.

BRIEF DESCRIPTION OF THE FIGURES

FIG. 1 shows the effect of substance-P on action potential (AP) characteristics of rabbit atrial myocytes. Atrial action potentials elicited at 1 Hz under control conditions and in the presence of 1 μM substance-P (SP) (FIG. 1A). Bar histograms showing average values for AP duration at 20.50 and 90% of repolarization ($APD_{20}$, $APD_{50}$, and $AP_{90}$) (FIG. 1B), resting membrane potential (RMP) and action potential amplitude (APA) (FIG. 1C), and maximal upstroke velocity ($V_{max}$) before (control) and after application of 1 μM SP (FIG. 1D). Plot showing the frequency-dependence of $APD_{90}$ before (control) and after application of 1 μM SP (FIG. 1E). Plot showing concentration-dependence of relative $APD_{90}$ before (control) and after application of increasing concentrations of SP (FIG. 1F). * P<0.05

FIG. 2 shows the absence of effect of NK1- and NK2 agonists on atrial action potential (AP) duration of rabbit atrial myocytes. Representative examples of atrial action potentials elicited at 2 Hz under control conditions and in the presence of 1 μM NK1-agonist [Sar9, Met (O2)11]-Substance P (FIG. 1A) or in the presence of 100 nM NK2-agonist (β-Ala)-Neurokinin A (4-10) (FIG. 1B, traces are superimposed). Bar histograms showing average values for AP duration at 90% of repolarization (APD90) before (control) and after application of increasing concentrations of [Sar9,Met (O2)11]-Substance P (FIG. 1C, n=6) or after application of increasing concentrations of (β-Ala)-Neurokinin A (4-10) (FIG. 1D, n=4). * P<0.05

FIG. 3 shows the action-potential prolonging effect of NK3-agonist Senktide on atrial action potential (AP) duration of rabbit atrial myocytes. Representative examples of atrial action potentials elicited at 2 Hz under control conditions and in the presence of 10 nM Senktide (FIG. 3A) Bar histograms showing average values for AP duration at 90% of repolarization (APD90) before (control) and after application of increasing concentrations of Senktide. FIG. 2B: 1-5 nM (n=4) and FIG. 2C: 10-100 nM (n=10). * P<0.05. Effects of Senktide on resting membrane potential (Vm) and upstroke velocity (Vmax) of the atrial action potential (FIG. 3D, 3E). Bar histograms showing average values for Vm (FIG. 3D) and Vmax (FIG. 3E) before (control) and after application of increasing concentrations of Senktide. The concentration groups 1-5 nM (n=4), 10-50 nM (n=10), and 100 nM (n=10) Senktide, have their own separate controls (black bars). *P<0.05

FIG. 5 shows the absence of effect of substance P and NK3-agonist Senktide on action potential (AP) duration of rabbit ventricular myocytes. Representative examples of ventricular action potentials elicited at 2 Hz under control conditions and in the presence of 10 μM substance-P (FIG. 5A) or in the presence of 100 nM NK3-agonist Senktide (FIG. 5B). Bar graphs showing average values for AP duration at 20.50 and 90% of repolarization (APD20, APD50, and APD90) before (control) and after application of 1 μM substance-P (FIG. 5C, n=7) or after application of 100 nM Senktide (FIG. 5D, n=4). * P<0.05

FIG. 7 shows increase in atrial effective refractory period in a rabbit Langendorff-perfused intact heart after application of the NK3-agonist (N-Me-Phe$^7$)-NKB (FIG. 7A-D). Unipolar electrograms recorded from the left atrium at a basic cycle length of 200 ms. 'A' and 'V' indicate atrial and ventricular activation resp. Under CTRL conditions the longest S1-S2 interval that fails to produce atrial activation is 75 ms (FIG. 7A,C (No Capture)). Application of 20 nM (N-Me-Phe$^7$)-NKB prolongs this interval to 105 ms (FIG. 7B,D (No Capture)).

FIG. 8 shows increase in atrial effective refractory period in vivo in the anesthetized rabbit after infusion of the NK3-agonist Senktide (FIG. 8A-D). Unipolar electrograms recorded from the left atrium at a basic cycle length of 220 ms. 'a' and 'v' indicate atrial and ventricular activation resp. At an S1-S2 interval of 170 ms, atrial activation can be elicited both under control conditions and in the presence of Senktide (FIG. 8A,B). Under CTRL conditions the longest S1-S2 interval that fails to produce atrial activation is 110 ms (FIG. 8C (No Capture)). Infusion of a single bolus of Senktide (11 nmol/kg) prolongs this interval to 160 ms (FIG. 8D (No Capture)).

FIG. 9 shows expression and localization of the neurokinin-3 receptor (NK3R) in left human atrial appendage. Sections of human atrial appendage show NK3R labeling (white) in the myocyte membrane (FIG. 9A) and not specifically in the nervous tissue in between myocytes (FIG. 9B).

FIG. 10 shows expression and localization of neurokinin B (NKB) in left human atrial appendage. Sections of human atrial appendage show NKB labeling in the nervous tissue within the myocardium (FIG. 10A, B).

DETAILED DESCRIPTION OF THE INVENTION

Definitions

Figure 4:
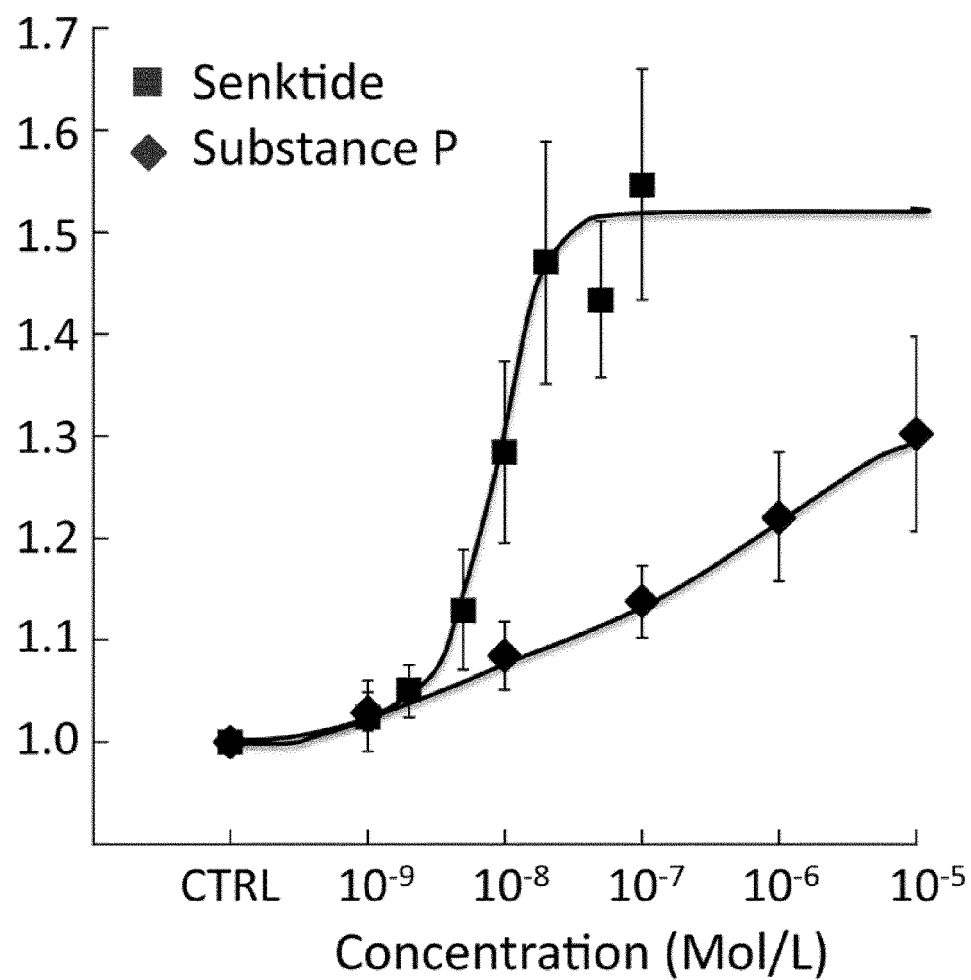
FIG. 4 shows the dose-response relationships for lengthening of atrial action potential duration by substance P and NK3-agonist Senktide. Plot showing concentration-dependence of relative APD90 before (control) and after application of increasing concentrations of substance P (black symbols, n=5) and Senktide (red symbols, n=4, n=10). * P<0.05. Data for 1-5 nM, 10-50 nM, and 100 nM Senktide have their own separate control (Black bar in FIG. 3B,C)

The term "agonist" is used herein to refer to a ligand that binds to a receptor and activates the receptor.

The term "NK3 receptor agonist" as used herein refers to a compound that causes activation of the NK3 receptor. The NK3 receptor agonist preferably has an affinity constant, Kj, of less than 50 nM, preferably less than 20 nM, and an in vitro intrinsic activity, measured as intracellular Ca2+ levels, greater than 20%, preferably greater than 50%, relative to 5-HT (1 μM). The term "NK3R agonist" or "NK3 agonist" as used herein refers to a compound capable of stimulating the Neurokinin 3 receptor (Tachykinin 3 receptor, Neurokinin B receptor).

The term "[Phe(Me)$^7$]neurokinin B" as used herein refers to a peptide having the amino acid sequence Asp-Met-His-Asp-Phe-Phe-(Me)Phe-Gly-Leu-Met-NH2 (SEQ ID NO:1).

The term "Neurokinine B" as used herein refers to a compound having CAS registry No. 86933-75-7.

The term "Senktide" as used herein refers to a compound having CAS registry No. 106128-89-6. IC50: Tachykinin receptor 3: EC50=0.5 nM (rat); NK3 receptor: EC50=3 nM (human); NK3 receptor: IC50=0.02 μM (human); Tachykinin receptor 3: IC50=0.01 μM (guinea pig).

The term "Neurokinine A" as used herein refers to a compound having CAS registry No. 86933-74-6.

The term "Substance P" as used herein refers to a compound having CAS registry No. 33507-63-0.

The term "Hemokinin 1" as used herein refers to a peptide having the amino acid sequence Arg-Ser-Arg-Thr-Arg-Gln-Phe-Tyr-Gly-Leu-Met-NH2 (SEQ ID NO:2).

The term "[Pro$^7$]neurokinin B" as used herein refers to a peptide having the amino acid sequence Asp-Met-His-Asp-Phe-Phe-Val-Gly-Leu-Met-NH2 (SEQ ID NO:3).

As used herein, the term "arrhythmia" refers to an abnormal heart beat as quantified by improper relationships between the P-Q-R-S-T electrocardiogram segments.

In the present invention, the term "abnormal electrical conduction" in cardiac muscle tissue can be used interchangeably with "re-entry," whereby electrical excitation occurring in cardiac muscle is not transmitted unidirectionally but rather turns in the vicinity of (excitation re-entry). Re-entry is classified as anatomical re-entry, which is caused by a specific heart tissue structure, and functional re-entry, which can occur at any cardiac muscle tissue site in the heart due to decreased cardiac muscle conduction at a local region and increased nonuniformity of refractory period (time during which, after electrical excitation of cardiac muscle cells occurs once, no response occurs even with an inflow of an electrical stimulus).

As used herein, the term "pharmaceutically acceptable salt" refers to a salt of a compound that is derived from a variety of physiologically acceptable organic and inorganic counter ions. Such counter ions are well known in the art and include, by way of example only, sodium, potassium, calcium, magnesium, aluminum, lithium and ammonium, for example tetraalkylammonium, and the like when the molecule contains an acidic functionality; and when the molecule contains a basic functionality, salts of organic or inorganic acids, such as hydrochloride, sulfate, phosphate, diphosphate, nitrate hydrobromide, tartrate, mesylate, acetate, malate, maleate, fumarate, tartrate, succinate, citrate, lactate, pamoate, salicylate, stearate, methanesulfonate, p-toluenesulfonate, and oxalate, and the like. Suitable pharmaceutically acceptable salts also include those listed in Remington's Pharmaceutical Sciences, 17th Edition, pg. 1418 (1985) and P. Heinrich Stahl, Camille G. Wermuth (Eds.), Handbook of Pharmaceutical Salts Properties, Selection, and Use; 2002. Examples of acid addition salts include those formed from acids such as hydroiodic, phosphoric, metaphosphoric, nitric and sulfuric acids, and with organic acids, such as alginic, ascorbic, anthranilic, benzoic, camphorsulfuric, citric, embonic (pamoic), ethanesulfonic, formic, fumaric, furoic, galacturonic, gentisic, gluconic, glucuronic, glutamic, glycolic, isonicotinic, isothionic, lactic, malic, mandelic, methanesulfonic, mucic, pantothenic, phenylacetic, propionic, saccharic, salicylic, stearic, succinic, sulfinilic, trifluoroacetic and arylsulfonic for example benzenesulfonic and p-toluenesulfonic acids. Examples of base addition salts formed with alkali metals and alkaline earth metals and organic bases include chloroprocaine, choline, N,N-dibenzylethylenediamine, diethanolamine, ethylenediamine, lysine, meglumaine (N-methylglucamine), and procaine, as well as internally formed salts. Salts having a non-physiologically acceptable anion or cation are within the scope of the invention as useful intermediates for the preparation of physiologically acceptable salts and/or for use in non-therapeutic, for example, in vitro, situations.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "susceptible" refers to a patient who has had at least one occurrence of the indicated condition.

The term "Atrial fibrillation" or "AF" as used herein refers to an abnormal contraction of an atrium which occurs when one or more of the heart's two upper chambers (the right and left atria) quiver instead of beating and contracting rhythmically. Electrocardiographically, AF is characterized by a highly disorganized atrial electrical activity that often results in fast beating of the heart's two lower chambers (the right and left ventricles). Symptoms experienced by patients with AF include palpitation, fatigue, and dyspnea (shortness of breath).

"Intravenous administration" is the administration of substances directly into a vein, or "intravenously". Compared with other routes of administration, the intravenous (IV) route is the fastest way to deliver fluids and medications throughout the body. An infusion pump can allow precise control over the flow rate and total amount delivered, but in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used, which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, a "flush", following the injection to push the medicine into the bloodstream more quickly.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical form for the oral administration of therapeutic agents includes the use of tablets or capsules.

NK3 Agonists for Use in the Treatment of Atrial Arrhythmia or AF

The inventors have shown that NK3 receptor agonists are suitable as atrial anti-arrhythmic drugs. They established that NK3 agonists prolong the atrial action potential by blockade of a background potassium current, and leave the ventricular action potential unaffected. Besides, NK3 receptor agonists are equally effective in prolonging atrial action potentials, at high and at low heart rates. Thus, the inventors have found in-vivo support that NK3 agonists have a high therapeutic effect in treating re-entry-based atrial arrhythmias as well as support based on well accepted ex-vivo models which have a demonstrated clinical relevance.

Therefore, in one embodiment an NK3 agonist for use in a method of treating or preventing an anti-arrhythmia is provided.

Any agonist of the NK3 receptor may be used. Agonists of the NK3 receptor are well known in the art. The NK3 agonist need not be a selective NK3 agonist and may also be a modulator of other Neurokinins, as long as it is capable of stimulating the Neurokinin 3 receptor. NK3 receptor agonists may suitably be identified by a skilled person by determining the affinity of a compound to the NK3 receptor by performing a radioligand binding assay, as described in Sarau et al., European Journal of Pharmacology 413 (2001). 143-150, on p 144. In addition, the capability of a compound to activate the NK3 receptor may be determined using a calcium mobilization assay, as described in Sarau et al., European Journal of Pharmacology 413 (2001). 143-150, on p 144-145. The results of the calcium mobilization assay described therein are reproduced herein in Table 2.

Examples of NK3 receptor agonist compounds useful in the invention are described herein and discussed more fully below. The NK3 receptor agonist may be any agonist of the Neurokinin 3 receptor. A non-limiting list of agonists of the Neurokinin 3 receptor include: Neurokinin B (NKB), Neurokinin A (NKA), Substance P (SP), Hemokinin 1 (HEK1), Eledoisin (non-mammalian tachykinin), Kassinin (non-mammalian tachykinin).

Preferably the agonist is N-(3-carboxy-1-oxopropyl)-L-α-aspartyl-L-phenylalanyl-N-methyl-L-phenylalanylglycyl-L-leucyl-L-methioninamide (Senktide). [125I]-[MePhe7] neurokinin B (specific activity, 2200 Ci/mmol), which may be obtained from New England Nuclear (Boston, Mass., USA). Neurokinin A, neurokinin B, substance P, [MePhe7]neurokinin B which may be obtained from Peninsula Laboratories (Belmont, Calif., USA) and senktide (succinyl-[Asp9MePhe8]-SP(6-13)) which may be obtained from California Peptide Research (Napa, Calif., USA).

In some embodiments, the compound is a high potency NK3 agonist that exhibits, for example, an IC$_{50}$ lower than about 0.1 µM, preferably lower than 0.09 µM, 0.08 µM, 0.07 µM, 0.06 µM, 0.05 µM, 0.04 µM, 0.03 µM, 0.02 µM, 0.01 µM for stimulation of a NK3 receptor.

In a preferred embodiment, said NK3 agonist has a EC$_{50}$ for the human NK3 receptor of at least 0.05 nM as determined in the Ca2+ mobilization assay as described in Sarau et al., European Journal of Pharmacology 413 (2001). 143-150. More preferably, said NK3 agonist has a EC$_{50}$ for the human NK3 receptor of at least 0.06, 0.07, 0.08, 0.09, 0.1 nM in the Ca2+ mobilization assay as described in Sarau et al., European Journal of Pharmacology 413 (2001). 143-150. In a preferred embodiment, said NK3 agonist is selected from the group consisting of Neurokinin B, (Neurokinin A), Hemokinin-1, Senktide, and [MePhe7]-NKB. In a preferred embodiment, said NK3 agonist is specific for NK3 and has a low affinity for other receptors such as for NK1 and NK2. Affinities of a number of compounds for NK1, NK2 and NK3 are summarized in Table 1.

The methods may include identifying a subject at risk for or suffering from atrial arrhythmia or AF or a condition associated with atrial arrhythmia or AF and administering a compound to the subject in an effective amount to treat or prevent the condition. The term "at risk for or suffering from" as used herein, refers to subjects suffering from chronic or paroxysmal AF or a condition associated with atrial arrhythmia or AF, including subjects currently experiencing an atrial arrhythmia or AF episode and those not currently experiencing an atrial arrhythmia or AF episode, as well as subjects who have not been diagnosed with atrial arrhythmia or AF, but who have been identified as being at risk for developing atrial arrhythmia or AF. Methods for identifying a subject at risk for or suffering from atrial arrhythmia or AF or a condition associated with atrial arrhythmia or AF are known in the art. Thus, in some embodiments, the compound is administered to a patient currently experiencing atrial arrhythmia or AF. In another embodiment, the compound is administered to a patient diagnosed with atrial arrhythmia or AF but not currently experiencing an atrial arrhythmia or AF episode. In still another embodiment, the compound is administered to a patient who has not been diagnosed with atrial arrhythmia or AF, but who has been identified as being at risk for developing atrial arrhythmia or AF. Risk factors of atrial arrhythmia or AF are well known in the art, and include, but are not limited to, increased age, high blood pressure, heart failure of almost any cause, congenital heart disease, coronary heart

TABLE 1

Affinity data of various ligands for the NK1-, NK2, and NK3-receptor

| Ligand | CAS Registry No. | NK-3 receptor Affinity | NK-3 receptor Units | NK-1 receptor Affinity | NK-1 receptor Units | NK2-receptor Affinity | NK2-receptor Units |
| --- | --- | --- | --- | --- | --- | --- | --- |
| Neurokinin A | 86933-74-6 | 5.5-6.3 | pK$_1$ | 6.2-9.3 | pK$_1$ | 8.0-9.1 | pK$_1$ |
|  |  | 7.4 | PEC$_{50}$ |  |  | 8.89 | pEC$_{50}$ |
| Neurokinin B | 86933-75-7 | 7.7-9.2 | pK$_1$ | 6.1-6.4 | pK1 | 5.0-7.7 | pK$_1$ |
| Substance P | 33507-63-0 | 5.0-6.0 | pK$_1$ | 8.5-10.3 | pK$_1$ | 5.9-6.9 | pK$_1$ |
| Hemokinin-1 |  | 8.6-9.3 | pK$_1$ | 9.8-11.7 | pK$_1$ | 6.3 | pK$_1$ |
| Eledoisin | 69-25-0 | 6.2-6.6 | pIC$_{50}$ | 8.6 | pIC$_{50}$ |  |  |
| Kassinin | 63968-82-1 | 6.7-7.0 | pIC$_{50}$ | 6.6-7.1 | pIC$_{50}$ |  |  |
| Senktide | 106128-89-6 | 7.1-9.1 | pK$_1$ |  |  |  |  |
|  |  | 7.9-8.8, 9.3 | pEC$_{50}$ |  |  |  |  |
| [Phe(Me)$^7$]-NKB |  | 8.7-9.6 | pK$_1$ |  |  |  |  |
|  |  | 8.9 | pEC$_{50}$ |  |  |  |  |
| [Pro]$^7$-NKB |  | 6.4-6.6 | pIC$_{50}$ |  |  |  |  |

TABLE 2

Ca$^{2+}$ mobilization of known NK3 agonists (reproduced from Sarau et al. 2001) Effects of tachykinin receptor ligands on [$^{125}$I]-[MePhe$^7$]neurokinin B binding and Ca$^{2+}$ mobilization in HEK 293-murine NK$_3$ receptor and HEK 293-human NK$_3$ receptor cells. The experimental protocols for these studies are given in Section 2.

| Agonists | Binding (Inhibition of[$^{125}$I]-[MePhe$^7$]neurokinin B) Murine NK$_3$ receptor, K$_i$ (nM) | Binding (Inhibition of[$^{125}$I]-[MePhe$^7$]neurokinin B) Human NK$_3$ receptor; K$_i$ (nM) | Ca$^{2+}$ Mobilization Murine NK$_3$ receptor, EC$_{50}$ (nM) | Ca$^{2+}$ Mobilization Human NK$_3$ receptor; EC$_{50}$ (nM) |
| --- | --- | --- | --- | --- |
| Neurokinin B | 2.3 ± 0.3 | 8.9 ± 0.2 | 0.09 ± 0.02 | 0.3 ± 0.2 |
| [MePhe$^7$]neurokinin B | 0.6 ± 0.1 | 1.8 ± 1.0 | 0.26 ± 0.13 | 0.3 ± 0.1 |
| Senktide | 11.9 ± 2.1 | 55 ± 19 | 0.15 ± 0.09 | 0.1 ± 0.03 |
| Neurokinin A | 785 ± 195 | 3300 ± 240 | 0.82 ± 0.24 | 22 ± 4 |
| Substance P | 4921 ± 2251 | 7660 ± 3090 | 5.4 ± 2.4 | 97 ± 16 |

Results are presented as EC$_{50}$ or K$_i$'s (for agonists) or IC$_{50}$ or K$_i$'s (for antagonists) and are the mean ± standard error of the mean or the mean: n = 3 unless indicated in parentheses. Some of the values for the experiments using HEK 293-human NK$_3$ receptor cells were taken from Sarau et al., 2000.

disease, including heart attack or myocardial infarction, abnormal heart muscle function, including congestive heart failure, disease of the mitral valve between the left and right ventricles, pericarditis, hyperthyroidism, overdose of thyroid medication, low amounts of oxygen in the blood, chronic lung diseases, including emphysema, asthma, or chronic obstructive pulmonary disease (COPD), pulmonary embolism, physical or psychological stress, excessive alcohol intake, stimulant drug use, such as cocaine or decongestants, diabetes and recent heart or lung surgery.

In an embodiment, the amount of substance P (and/or neurokinins A and B) is determined in a body fluid of a patient to determine the concentration and/or the dosage regime of said NK3 agonist in the treatment of atrial arrhythmia or AF. By measuring substance P (and/or neurokinins A and B) in for instance serum of patients with atrial fibrillation, support for the underlying mechanisms (re-entry or not re-entry) can be found. This can help guiding therapy (the isolation of pulmonary veins or the structural alteration of the atrial myocardium): the higher the substance P (neurokinins A/B) level the lower the chance that the arrhythmia is re-entrant.

Said NK3 agonist may be administered to the patient by known enteral or parenteral routes, including but not limited to oral administration (such as oral gavage, sublingual administration or rectal administration), injection directly into the blood stream (such as intravenous or intra-arterial administration), or various parenteral routes (such as intraperitoneal and subcutaneous routes such as intramuscular), respiratory-based administration via an aerosol, and administration under the skin (i.e., transdermal, transcutaneous or percutaneous), as well as topical administration of the formulated compound of interest. A preferred form of administration of the NK3 agonist is the oral (PO) administration, intravenous or the intraperitoneal (IP) administration. Preferably, the NK3 agonist is administered at a single dose.

A preferred subject is a mammal. A mammal may include any mammal. As a non-limiting example, preferred mammals include cattle, pigs, sheep, goats, horses, camels, buffalo, cats, dogs, guinea pigs, rats, mice, and humans. A highly preferred subject mammal is a human. The compound(s) may be administered to the subject via any drug delivery route known in the art, including for example, but not limited to, oral, ocular, rectal, buccal, topical, nasal, ophthalmic, subcutaneous, intramuscular, intravenous (bolus and infusion), intracerebral, transdermal, and pulmonary.

In said method of treatment of the invention, said NK3 agonist is used in a therapeutically effective amount or prophylactically effective amount. The terms "therapeutically effective amount" and "prophylactically effective amount," as used herein, refer to an amount of a compound sufficient to treat (e.g. ameliorate or prevent) the identified disease or condition, or to exhibit a detectable therapeutic, prophylactic, and/or agonistic effect. For example, the effect may be restoration of normal sinus rhythm, reduction of atrial arrhythmia or AF burden, either in time spent in atrial arrhythmia or AF or in duration of atrial arrhythmia or AF episodes, reduction in atrial fibrosis, suppression of atrial arrhythmia or AF, termination of atrial arrhythmia or AF, inhibition of atrial arrhythmia or AF, prevention of recurrence of atrial arrhythmia or AF, prevention of developing atrial arrhythmia or AF, and the like. The effect may be detected by any means known in the art. The precise effective amount for a subject will depend upon the subject's body weight, size, and health; the nature and extent of the condition; and the therapeutic or combination of therapeutics selected for administration. Therapeutically and prophylactically effective amounts for a given situation may be determined by routine experimentation that is within the skill and judgment of the clinician.

For any compound, the therapeutically or prophylactically effective amount may be estimated initially either in cell culture assays or in animal models, usually rats, mice, rabbits, dogs, or pigs. The animal model may also be used to determine the appropriate concentration range and route of administration. Such information may then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it may be expressed as the ratio, $ED_{50}/LD_{50}$. Pharmaceutical compositions that exhibit large therapeutic indices are preferred. However, the pharmaceutical compositions that exhibit narrow therapeutic indices are also within the scope of the embodiments. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

In preferred embodiments, the maximum plasma concentrations ($C_{max}$) may range from about 1 pg/ml to about 200 pg/ml, preferably around 20 pg/ml depending upon the route of administration. In general the dose will typically be in the range of about 100 mg/day to about 10 g/day, or about 200 mg to about 5 g/day, or about 400 mg to about 3 g/day, or about 500 mg to about 2 g/day, in single, divided, or continuous doses for a patient weighing between about 40 to about 100 kg (which dose may be adjusted for patients above or below this weight range, particularly children under 40 kg). Generally, the dose will be in the range of about 25 mg/kg to about 300 mg/kg of body weight per day. In one embodiment, the NK3 agonist compound is administered to the subject in a unit dosage form comprising about 100 to about 400 mg of the NK3 agonist compound per dose. In another embodiment, the dosing is between 2.56 and 5.12 nmol/kg/h. The dosing may be once, or twice or three times daily, with one or more units per intake. According to one embodiment, the total daily intake is at least about 1200 mg of the NK3 agonist compound.

The exact dosage will typically be determined by the practitioner, in light of factors related to the subject that requires treatment. Dosage and administration are generally adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In one aspect, treating atrial arrhythmia or AF results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating atrial arrhythmia or AF results in a decrease in the mortality rate of a population of treated subjects in comparison to a population of subjects receiving carrier alone. In another aspect, treating atrial arrhythmia or AF results in a decrease in the mortality rate of a population of treated subjects in comparison to an untreated population. In a further aspect, treating atrial arrhythmia or AF results a decrease in the mortality rate of a population of treated subjects in comparison to a population receiving monotherapy with a drug that is not a compound of the embodiments, or a pharmaceutically acceptable salt, metabolite, analog or derivative thereof. Preferably, the mortality rate is decreased by more than about 2%; more preferably, by more than about 5%; more preferably, by more than about 10%; and most preferably, by more than about 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease related deaths per unit time following completion of a first round of treatment with an active compound.

In another aspect, treating atrial arrhythmia or AF results in a decrease in atrial arrhythmia or AF burden, either time spent in atrial arrhythmia or AF or duration of atrial arrhythmia or AF episodes. Preferably, after treatment, the atrial arrhythmia or AF burden is reduced by at least about 5% relative to the atrial arrhythmia or AF burden prior to treatment; more preferably, atrial arrhythmia or AF burden is reduced by at least about 10%; more preferably, reduced by at least about 20%; more preferably, reduced by at least about 30%; more preferably, reduced by at least about 40%; more preferably, reduced by at least about 50%; even more preferably, reduced by at least 60%; reduced by at least 75%; and most preferably, reduced by at least about 100%, atrial arrhythmia or AF burden may be measured by any reproducible means of measurement. In a preferred aspect, atrial arrhythmia or AF burden is measured using an electronic recording device.

In one embodiment, atrial fibrosis in a subject is reduced following administration of a NK3 agonist compound relative to prior to administration of the NK3 agonist compound. In some embodiments, the atrial fibrosis is reduced by more than about 2%; more than about 5%; more than about 10%; or more than about 25%. In some aspects, a reduction of atrial fibrosis of a population of treated subjects may be measured by any reproducible means. For example, a reduction in atrial fibrosis may be measured by EP study, MRI, CAT scan, and the like.

The methods described herein may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification. Examples include, but are not limited to, listening to the subject's heart beat, taking the subject's pulse, an electrocardiogram (EKG), a Holter monitor or other similar device for the continuous recording of the heart rhythm, a patient-activated or automatically-triggered event recorder or other similar device whereby the subject's heart rhythm is recorded at the onset of symptoms, echocardiography, ultrasound, transesophageal echocardiography (TEE), electrophysiologic (EP) studies, and the like. In addition, high blood pressure and signs of heart failure may be ascertained during a physical examination of the subject.

Blood tests may be performed to detect abnormalities in blood oxygen and carbon dioxide levels, electrolytes, and thyroid hormone levels. Chest x-rays, CAT scans, and MRI may reveal enlargement of the heart, heart failure, and other diseases of the lung. Exercise treadmill testing may be used to detect severe coronary artery disease.

Composition for Use in the Treatment of Atrial Arrhythmia or AF

As described elsewhere herein, the compounds described herein may be formulated in pharmaceutical compositions, if desired, and may be administered by any route that permits treatment of the disease or condition. A preferred route of administration is oral administration. Administration may take the form of single dose administration, or the compound of the embodiments may be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

The methods of the embodiments also include the use of a compound or compounds as described herein together with one or more additional therapeutic agents for the treatment of disease conditions. Additional therapeutic agents for the treatment of atrial arrhythmia or AF are well-known in the art and include, for example, digoxin, beta blockers (atenolol, metoprolol, propranolol), amiodarone, disopyramide, calcium antagonists (verapamil, diltiazam), sotalol, flecanaide, procainamide, quinidine and propafenone. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In addition, embodiments of the invention include the use of a compound or compounds as described herein together with one or more atrial arrhythmia or AF therapies, atrial arrhythmia or AF therapies are well-known in the art, and include, for example, anti-arrhythmic therapy, electrical cardioversion, surgical procedures, such as the Maze procedure, ablation, radiofrequency energy, atrial pacemakers, and the like. Thus, for example, the compounds described herein may be administered before, during or after one or more atrial arrhythmia or AF therapies.

The above disclosure generally describes the present invention. Unless defined otherwise, all technical and scientific terms used herein have the same meaning as those commonly understood by one of ordinary skill in the art to which this invention belongs. A more complete understanding can be obtained by reference to the following specific examples which are provided herein for purposes of illustration only, and are not intended to limit the scope of the invention.

Example Section

The effect of substance-P on action potential (AP) characteristics was tested in vitro in rabbit atrial myocytes. Atrial action potentials elicited at 1 Hz under control conditions and in the presence of 1 µM substance-P (SP) (FIG. 1A). Bar histograms showing average values for AP duration at 20.50 and 90% of repolarization ($APD_{20}$, $APD_{50}$, and $APD_{90}$) (FIG. 1B), resting membrane potential (RMP) and action potential amplitude (APA) (FIG. 1C), and maximal upstroke velocity ($V_{max}$) before (control) and after application of 1 µM SP (FIG. 1D). Plot showing the frequency-dependence of $APD_{90}$ before (control) and after application of 1 µM SP (FIG. 1E). Plot showing concentration-dependence of relative $APD_{90}$ before (control) and after application of increasing concentrations of SP (FIG. 1F). * $P<0.05$. In conclusion, Substance P significantly prolongs the AP duration in single rabbit atrial myocytes in a dose-dependent manner, also at high stimulation frequencies.

Further, it was tested to confirm that the NK1 and NK2 receptor is not responsible for prolongation of atrial action potential (AP) duration. FIG. 2 shows the absence of effect of NK1- and NK2 agonists on atrial action potential (AP) duration of rabbit atrial myocytes. Representative examples of atrial action potentials elicited at 2 Hz under control conditions and in the presence of 1 µM NK1-agonist [Sar9, Met (O2)11]-Substance P (FIG. 1A) or in the presence of 100 nM NK2-agonist (β-Ala)-Neurokinin A (4-10) (FIG. 1B, traces are superimposed). Bar histograms showing average values for AP duration at 90% of repolarization (APD90) before (control) and after application of increasing concentrations of [Sar9,Met (O2)11]-Substance P (FIG. 1C, n=6) or after application of increasing concentrations of (β-Ala)-Neurokinin A (4-10) (FIG. 1D, n=4). * $P<0.05$. In conclusion, stimulation of the NK1- and NK2-receptor does not affect AP duration in rabbit atrial myocytes. Therefore, the observed prolongation of atrial action potential (AP) duration may be attributed to activation of the NK3 receptor.

Subsequently, the dose response relation of NK3-agonist Senktide was determined in rabbit atrial myocytes. FIG. 3 shows the action-potential prolonging effect of Senktide on atrial action potential (AP) duration of rabbit atrial myocytes. Representative examples of atrial action potentials elicited at 2 Hz under control conditions and in the presence of 10 nM Senktide (FIG. 3A) Bar histograms showing average values for AP duration at 90% of repolarization (APD90) before (control) and after application of increasing concentrations of Senktide. FIG. 2B: 1-5 nM (n=10) and FIG. 2C: 10-100 nM (n=10, n=16). * $P<0.05$. Effects of Senktide on resting membrane potential (Vm) and upstroke velocity (Vmax) of the atrial action potential (FIG. 3D, 3E). Bar histograms showing average values for Vm (FIG. 3D) and Vmax (FIG. 3E) before (control) and after application of increasing concentrations of Senktide. The concentration groups 1-5 nM (n=10), 10-50 nM (n=10), and 100 nM (n=16) Senktide, have their own separate controls (black bars). *$P<0.05$ In conclusion, stimulation of the NK3-receptor by Senktide significantly prolongs the AP duration in rabbit atrial myocytes in a dose-dependent manner, mimicking the effect of Substance P. Thus, the AP prolonging-effect of Substance P on atrial myocytes is mediated through stimulation of the NK3-receptor.

FIG. 4 shows the dose-response relationships for lengthening of atrial action potential duration by substance P and NK3-agonist Senktide. Plot showing concentration-dependence of relative APD90 before (control) and after application of increasing concentrations of substance P (black symbols, n=5) and Senktide (red symbols, n=10, n=16). * $P<0.05$. Data for 1-5 nM, 10-50 nM, and 100 nM Senktide have their own separate control (Black bar in FIG. 3B,C) In conclusion, the selective NK3-receptor agonist Senktide is several orders of magnitude more potent than Substance P in prolonging the atrial AP.

Further, it was determined whether the effect AP-prolonging effect by NK3 agonists is atrium-specific. FIG. 5 shows the absence of effect of substance P and NK3-agonist Senktide on action potential (AP) duration of rabbit ventricular myocytes. Representative examples of ventricular action potentials elicited at 2 Hz under control conditions and in the presence of 10 µM substance-P (FIG. 5A) or in the presence of 100 nM NK3-agonist Senktide (FIG. 5B). Bar graphs showing average values for AP duration at 20.50 and 90% of repolarization (APD20, APD50, and APD90) before (control) and after application of 1 µM substance-P (FIG. 5C, n=7) or after application of 100 nM Senktide (FIG. 5D, n=4). * $P<0.05$ In conclusion, stimulation of the NK3-receptor by Substance P or Senktide does not prolong the AP in ventricular myocytes, indicating that the AP-prolonging effect is atrial-specific. Consequently, NK3-receptor agonists lack a proarrhythmic action in ventricle, as frequently observed for other atrial AP-prolonging drugs.

Figure 6:
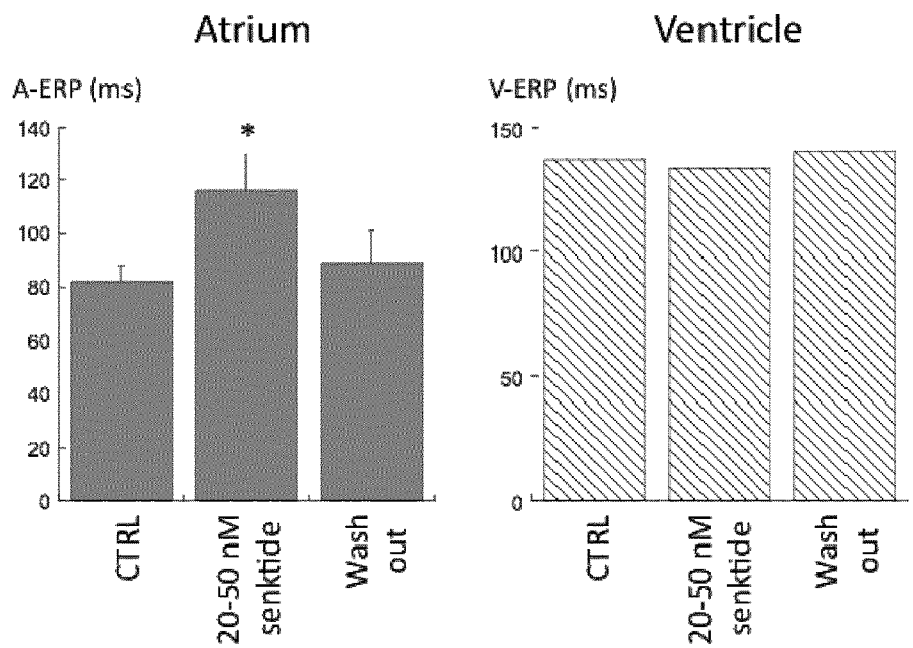
FIG. 6 shows increase in atrial effective refractory period in intact Langendorff-perfused rabbit hearts after application of the NK3-agonist Senktide (FIG. 6A-E). Unipolar electrograms recorded from the left atrium at a basic cycle length of 200 ms. 'A' and 'V' indicate atrial and ventricular activation resp. Under CTRL conditions the longest S1-S2 interval that fails to produce atrial activation is 80 ms (FIG. 6a,c (No Capture)). Application of 750 nM Senktide prolongs this interval to 100 ms (FIG. 6b,d (No Capture)). Bar histograms showing average values for atrial effective refractory (A-ERP, FIG. 6E, left panel, n=5) and ventricular effective refractory period (V-ERP, FIG. 6E, right panel, n=3) before (control) and after application of 20-50 nM Senktide. V-ERP was not affected by Senktide. * P<0.05.

Further, it was determined whether Senktide also prolongs the atrial effective refractory period in ex-vivo intact hearts. FIG. 6 shows increase in atrial effective refractory period in intact Langendorff-perfused rabbit hearts after application of the NK3-agonist Senktide (FIG. 6A,B). Unipolar electrograms recorded from the left atrium at a basic cycle length of 200 ms. 'A' and 'V' indicate atrial and ventricular activation resp. Under CTRL conditions the longest S1-S2 interval that fails to produce atrial activation is 80 ms (FIG. 6Aa,c (No Capture)). Application of 750 nM Senktide prolongs this interval to 100 ms (FIG. 6Ab,d (No Capture)). Bar histograms showing average values for atrial effective refractory (A-ERP, FIG. 6B, left panel, n=5) and ventricular effective refractory period (V-ERP, FIG. 6B, right panel, n=3) before (control) and after application of 20-50 nM Senktide. V-ERP was not affected by Senktide. * $P<0.05$.

In conclusion, Senktide prolongs the atrial refractory period in the Langendorff-perfused rabbit heart, indicating that stimulation of the NK3-receptor prolongs the AP also in the intact heart.

Further, it was determined whether NK3-agonist (N-Me-Phe[7])-NKB also prolongs the atrial effective refractory period in ex-vivo intact hearts. FIG. 7 shows increase in atrial effective refractory period in a rabbit Langendorff-perfused intact heart after application of the NK3-agonist (N-Me-Phe[7])-NKB (FIG. 6A-D). Unipolar electrograms recorded from the left atrium at a basic cycle length of 200 ms. 'A' and 'V' indicate atrial and ventricular activation resp. Under CTRL conditions the longest S1-S2 interval that fails to produce atrial activation is 75 ms (FIG. 6A,C (No Capture)). Application of 20 nM (N-Me-Phe[7])-NKB prolongs this interval to 105 ms (FIG. 6B,D (No Capture)). In conclusion, in addition to Substance P and Senktide, the (N-Me-Phe[7])-NKB also prolongs the atrial effective refractory period, indicating that prolongation of the atrial AP is a feature of NK3-receptor agonists in general.

Next, it was tested whether Senktide the AP-prolonging effect of the NK3-receptor agonist Senktide is preserved in vivo. FIG. 8 shows increase in atrial effective refractory period in vivo in the anesthetized rabbit after infusion of the NK3-agonist Senktide (FIG. 8A-D). Unipolar electrograms recorded from the left atrium at a basic cycle length of 220 ms. 'a' and 'v' indicate atrial and ventricular activation resp. At an S1-S2 interval of 170 ms, atrial activation can be elicited both under control conditions and in the presence of Senktide (FIG. 8A,B). Under CTRL conditions the longest S1-S2 interval that fails to produce atrial activation is 110 ms (FIG. 8C (No Capture)). Infusion of a single bolus of Senktide (11 nmol/kg) prolongs this interval to 160 ms (FIG. 8D (No Capture)). In conclusion, the AP-prolonging effect of the NK3-receptor agonist Senktide as observed in vitro in single myocytes and Langendorff-perfused hearts, is preserved in vivo.

Further, the expression and localization of the neurokinin-3 receptor (NK3R) in left human atrial appendage was determined (FIG. 9). Sections of human atrial appendage show NK3R labeling (white) in the myocyte membrane (FIG. 9A) and not specifically in the nervous tissue in between myocytes (FIG. 9B). In conclusion, myocytes of human left atrial appendage express the NK3R in their cell membranes.

FIG. 10 shows expression and localization of neurokinin B (NKB) in left human atrial appendage. Sections of human atrial appendage show NKB labeling in the nervous tissue within the myocardium (FIG. 10A, B).

In conclusion, the natural NK3-receptor agonist NKB is produced by the intracardiac nerves in human atrial tissue.

Figure 11:
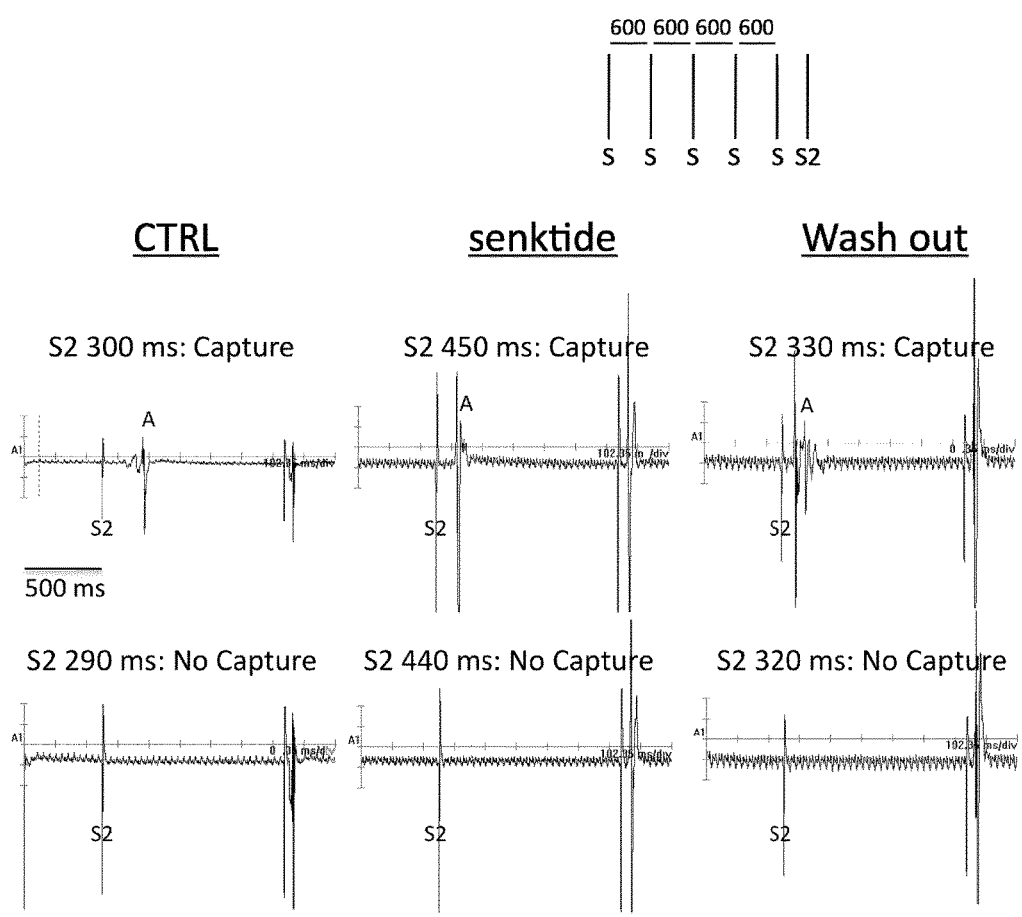
FIG. 11 shows increase in atrial effective refractory period in human left atrial appendage (LAA) after application of the NK3-agonist Senktide. Unipolar electrograms recorded from the LAA at a basic cycle length of 600 ms. 'A' indicates atrial activation. Under CTRL conditions the longest S1-S2 interval that fails to produce atrial activation is 290 ms (FIG. 11, left panel). Application of 50 nM Senktide prolongs this interval to 440 ms (FIG. 11, middle panel). Wash out partly restores the effective refractory periods to 320 ms (right panel).

Further, it was tested whether the NK3-receptor is functionally present in human atrium. FIG. 11 shows increase in atrial effective refractory period in human left atrial appendage (LAA) after application of the NK3-agonist Senktide. Unipolar electrograms recorded from the LAA at a basic cycle length of 600 ms. 'A' indicates atrial activation. Under CTRL conditions the longest S1-S2 interval that fails to produce atrial activation is 290 ms (FIG. 11, left panel). Application of 50 nM Senktide prolongs this interval to 440 ms (FIG. 11, middle panel). Wash out partly restores the effective refractory periods to 320 ms (right panel). In conclusion, Senktide prolongs the effective refractory period also in human LAA, indicating that the NK3-receptor is functionally present in human atrium.

Single Cell Preparation

Male New Zealand White specified pathogen free rabbits (2.5-3.5 kg) were anaesthetized with a combination of 20 mg xylazine and 100 mg ketamine (intramuscularly) and heparinized with a bolus of 1000 IU heparin (intravenously). Subsequently, the animals were killed by 200 mg pentobarbital intravenously, after which the heart was quickly excised and mounted on a langendorff perfusion apparatus. Single ventricular cells were isolated from the left ventricle by enzymatic dissociation using the protocol that was described previously [7]. Single atrial cells were isolated from the left atrium using the same protocol with a modification consisting of complementing the enzymatic solution with 6.6 pg/mL protease.

Small aliquots of single cell suspension were introduced into a recording chamber on the stage of an inverted microscope. Cells were allowed to adhere for 5 minutes after which superfusion was started. Single quiescent rod-shaped myocytes with clear cross-striations and smooth surfaces were selected for measurements.

Cellular Electrophysiology
Data Acquisition and Analysis

APs were recorded at 36.5° C. with the amphotericin-B-perforated patch-clamp technique, using an Axopatch 200B Clamp amplifier (Molecular Devices Corporation, Sunnyvale, Calif., USA). Voltage control, data acquisition, and analysis were performed using custom-made software.

Potentials were corrected for liquid junction potential [3]. Signals were low-pass filtered (cut-off frequency: 5 kHz) and digitized at 40 kHz. Cell membrane capacitance ($C_m$) was estimated by dividing the decay time constant of the capacitive transient in response to 5 mV hyperpolarizing voltage clamp steps from a holding potential of −40 mV, by the series resistance.

Current-Clamp Experiments

APs were measured with the amphotericin-B-perforated patch clamp technique using normal Tyrode's solution containing (in mM): NaCl 140, KCl 5.4, $CaCl_2$ 1.8, $MgCl_2$ 1.0, glucose 5.5, HEPES 5.0, pH 7.4 (NaOH). The patch-pipettes (borosilicate glass; 1-3 MΩ) were filled with a 'standard' solution containing (in mM): K-gluconate 110, KCl 30, NaCl 5, $MgCl_2$ 1, amphotericin-B 0.22, HEPES 10, pH 7.3 (KOH).

APs were elicited at 2 Hz by 2-ms (1.5×diastolic stimulation threshold) current pulses applied through the patch pipette. The following action potential characteristics were determined: resting membrane potential (RMP), maximal upstroke velocity ($V_{max}$), AP amplitude (APA), and AP duration (APD) at 20%, 50% and 90% repolarization ($APD_{20}$, $APD_{50}$ and $APD_{90}$, respectively). Values obtained from 10 consecutive APs were averaged.

Atrial and ventricular myocytes were allowed to equilibrate for a 5-minute period of continuous stimulation (2 Hz) after which the wash-in of the following neuropeptides and neurokinin (NK) agonists: substance P (SP, Emelca Biosdence artnr 350394), NK1-agonist [$Sar^9$, $Met(O_2)^{11}$]-Substance P (SAR-SP, Sigma 53672), NK2-agonist-ala8-neurokinin A (4-10) (Bachem H-2786) and NK3-agonist Senktide ([Succinyl-$Asp^6$,Me-$Phe^8$]-Senktide Substance P 6-11, Sigma SCP0238), was started. The NK-agonists were applied in a cumulative sequence with 5 minutes intervals between increments in concentration. Effects were assessed after equilibration, but not earlier than 3 minutes after application.

Measurement of Left Atrial and Ventricular Effective Refractory Period (ERP) in Langendorff-Perfused Rabbit Hearts:

After the heart was excised, it was cannulated, quickly mounted on a Langendorff perfusion set-up, and perfused at 37° C. with a solution containing (in mmol/L) 128 NaCl, 4.7 KCl, 1.45 $CaCl_2$), 0.6 MgCl2, 27 $NaHCO_3$, 0.4 NaH2PO4, and 11 glucose (pH maintained at 7.4 by equilibration with a mixture of 95% 02 and 5% CO2). The left atrium (ventricle) was stimulated at a basic cycle length of 200 ms, and twice the diastolic stimulus current threshold. The effective refractory period (ERP) was determined by a train of 16 stimuli at 200 ms followed by a single stimulus with progressively shortened coupling interval until the left atrium (ventricle) failed to be activated. The effective refractory period was defined as the longest S1-S2 interval failing to produce atrial (ventricular) activation. After an equilibrium period of 30 min., wash in of the NK3-agonists Senktide or (N-Me-Phe7)-neurokinin B (Sigma) was started.

In Vivo Measurement of Left Atrial Effective Refractory Period (A-ERP) in the Anesthetised Rabbit:

Male New Zealand White rabbits were anesthetized with ketamine 50 mg/kg and xylazine 8 mg/kg (and additionally 0.09 mg/kg Temgesic for pain relief) subcutaneously, intubated, and artificially ventilated. Anesthesia was maintained by isoflurane (0.8-1.2%). Catheters for drug infusions and blood pressure recording were inserted into marginal ear veins/arteries. Following thoracotomy, the pericardium was opened to expose the heart. A stimulation- and recording-electrode were placed on the left atrium for epicardial electrophysiological study. The left atrium was stimulated at a basic cycle length of 220 ms, and twice the diastolic stimulus current threshold. The effective refractory period (ERP) was determined by a train of 8 stimuli at 220 ms followed by a single stimulus with progressively shortened coupling interval until the left atrium failed to be activated. The effective refractory period was defined as the longest S1-S2 interval failing to produce atrial activation. Approximately 30 minutes after the completion of the preparation when the rabbit was hemodynamically and electrophysiologically stable, control measurements were undertaken. Subsequently, a single bolus injection (1 ml) of 11 nmol/kg Senktide was administered.

Measurement of Effective Refractory Period in Human Left Atrial Appendages:

Left atrial appendages (LAA) were routinely removed from patients with atrial fibrillation receiving PVI (pulmonary vein isolation) ablation. The LAAs were removed using an endoscopic stapling device (Endo Gia stapler, Tyco Healthcare Group). The tissue samples were transported in 100-mL cooled superfusion fluid ($Na^+$, 155.5 mmol/L; $K^+$, 4.7 mmol/L; $Ca^{2+}$, 1.45 mmol/L; $Mg^{2+}$, 0.6 mmol/L; $Cl^-$, 136.6 mmol/L; $HCO_3^-$, 27 mmol/L; $PO_4^{3-}$, 0.4 mmol/L; glucose, 11.1 mmol/L; and heparin, 1000 IE) and submerged in a tissue bath. The superfusion fluid was kept at a stable temperature of 36.5° C. to 37.5° C. and oxygenized with a mixture of 95% $O_2$ and 5% $CO_2$ to maintain a pH of 7.4. LAAs were stimulated at 100 beats per minute at 2-3 times diastolic threshold with a pulse width of 2 ms using an epicardial electrode.

The effective refractory period (ERP) was determined by a train of 8 stimuli (at 600 ms interval) followed by a single stimulus with progressively shortened coupling interval until the LAA failed to be activated. The effective refractory period was defined as the longest S1-S2 interval failing to produce atrial (ventricular) activation. After an equilibrium period of 30 min., wash in of the NK3-agonists Senktide was started.

Antibodies

For immunohistochemistry, the following primary antibodies were used: polyclonal anti-NK3R (Santa Cruz sc-28952; 1:20 dilution), polyclonal anti-NKB (Santa Cruz sc-292436; 1:50), monoclonal anti-α-actinin (Sigma T7811; 1:1000), monoclonal anti-β-Tubulin II (Sigma T8660, 1:200). Alexa-conjugated goat anti-mouse and goat anti-rabbit secondary antibodies were used (1:250, Molecular Probes, Invitrogen).

Immunohistochemistry

Human left atrial appendages were snap-frozen in liquid nitrogen, and stored at −80° C. Cryosections (7 μm) were mounted on 3-aminopropyltriethoxysilane (AAS)-coated glass slides and permeabilized in 0.2% Triton X-100 in PBS for 1 hour. Subsequently, cryosections were blocked in 2% bovine serum albumin for 30 minutes and incubated with primary (overnight) and secondary antibody (90 minutes) in 10% NGS (at room temperature). For double labeling, sections were incubated with a mixture of primary antibodies, followed by an appropriate mixture of secondary antibodies. Confocal imaging was performed using a confocal laser scanning microscope (BioRad MRC1024) equipped with a 15-mV Krypton/Argon laser, using the 568 and 488 excitation lines and 605DF32 and 522DF35 emission filters.

Statistics

Data are presented as mean±SEM. A student t-test was used and $P<0.05$ was defined as statistical significant.

REFERENCES

[3] Barry P H, Lynch J W (1991) Liquid junction potentials and small cell effects in patch-clamp analysis. J Membr Biol 121:101-117 doi: 10.1007/BF01870526

[7] Den Ruijter H M, Verkerk A O, Coronel R (2010) Incorporated fish oil fatty acids prevent action potential shortening induced by circulating fish oil fatty acids. Front Physiol 1:149 doi: 10.3389/fphys.2010.00149

The invention claimed is:

1. A method for treating atrial arrhythmia comprising administering to a subject in need thereof an NK3 agonist selected from the group consisting of Neurokinin B (NKB), Neurokinin A (NKA), Hemokinin 1 (HEK1), Eledoisin, Kassinin, Senktide [succinyl-(Asp6, MePhe8)-SP(6-11)], [MePhe7]-NKB (1a), Pro7-NKB, and a pharmaceutically acceptable salt thereof.

2. The method according to claim 1, wherein said NK3 agonist is selected from the group consisting of Neurokinin B (NKB), Pro7-NKB, Neurokinin A (NKA) and Senktide.

3. The method according to claim 1, wherein said NK3 agonist is formulated in a composition comprising a pharmaceutically acceptable carrier.

4. The method according to claim 3, wherein said composition is formulated for intravenous administration.

5. The method according to claim 4, wherein said NK3 agonist is selected from the group consisting of Neurokinin B (NKB), Pro7-NKB, Neurokinin A (NKA) and Senktide.

6. The method according to claim 3, wherein said composition is formulated for oral administration.

7. The method according to claim 6, wherein the NK3 agonist is selected from the group consisting of Neurokinin B (NKB), Pro7-NKB, Neurokinin A (NKA) and Senktide.

8. The method according to claim 3, wherein said NK3 agonist is selected from the group consisting of Neurokinin B (NKB), Pro7-NKB, Neurokinin A (NKA) and Senktide.

9. The method according to claim 3, wherein said subject is a human.

10. The method according to claim 3, wherein said NK3 agonist is Neurokinin B (NKB).

11. The method according to claim 3, wherein said NK3 agonist is Pro7-NKB.

12. The method according to claim 3, wherein said NK3 agonist is Neurokinin A (NKA).

13. The method according to claim 3, wherein said NK3 agonist is Senktide.

14. The method according to claim 3, wherein said NK3 agonist is Neurokinin B (NKB), Pro7-NKB, Neurokinin A (NKA) and Senktide.

15. The method according to claim 3, further comprising administering one or more additional therapeutic agent to the subject.

16. The method according to claim 15, wherein the one or more additional therapeutic agent is selected from the group consisting of digoxin, beta blockers, amiodarone, disopyramide, calcium antagonists, Sotalol, flecanaide, procainamide, quinidine and propafenone.

17. The method according to claim 15, wherein the NK3 agonist and the one or more additional therapeutic agent are administered simultaneously.

18. The method according to claim 15, comprising administering sequentially to the subject the NK3 agonist, followed by the one or more additional therapeutic agent.

19. The method according to claim 15, comprising administering sequentially to the subject the one or more additional therapeutic agent, followed by the NK3 agonist.

20. A method for treating a disease caused by abnormal electrical conduction in the atrial muscle tissue of a subject, comprising administering to the subject an NK3 agonist selected from the group consisting of Neurokinin B (NKB), Neurokinin A (NKA), Hemokinin 1 (HEK1), Eledoisin, Kassinin, Senktide [succinyl-(Asp6, MePhe8)-SP(6-11)], [MePhe7]-NKB (1a), Pro7-NKB, and a pharmaceutically acceptable salt thereof.

* * * * *